(12) United States Patent
Southerland, III et al.

(10) Patent No.: US 11,284,818 B2
(45) Date of Patent: Mar. 29, 2022

(54) GLUCOSE EXPOSURE DIAGNOSTICS AND THERAPEUTICS RELATED THERETO

(71) Applicant: TT1 Products, Inc., Atlanta, GA (US)

(72) Inventors: Harold Philpott Southerland, III, Atlanta, GA (US); Todd Furneaux, Atlanta, GA (US); Juan Pablo Frais, Atlanta, GA (US); Roger Steven Mazze, Exclesior, MN (US)

(73) Assignee: TT1 Products, Inc., Atlanta, GA (US)

( * ) Notice: Subject to any disclaimer, the term of this patent is extended or adjusted under 35 U.S.C. 154(b) by 0 days.

(21) Appl. No.: 17/008,220

(22) Filed: Aug. 31, 2020

(65) Prior Publication Data

US 2022/0061708 A1 Mar. 3, 2022

(51) Int. Cl.
*A61B 5/145* (2006.01)
*A61B 5/00* (2006.01)
*G16H 40/63* (2018.01)
*G16H 40/67* (2018.01)

(52) U.S. Cl.
CPC ........ *A61B 5/14532* (2013.01); *A61B 5/0004* (2013.01); *A61B 5/4839* (2013.01); *A61B 5/742* (2013.01); *G16H 40/63* (2018.01); *G16H 40/67* (2018.01)

(58) Field of Classification Search
CPC . A61B 5/14532; A61B 5/145; A61B 5/14503; A61B 5/14507; A61B 5/1451; A61B 5/14517; A61B 5/14525; A61B 5/14528; A61B 5/0004; A61B 5/0002; A61B 5/002; A61B 5/0022; A61B 5/0036; A61B 5/4839; A61B 5/742; A61B 5/4833; A61B 5/4836; A61B 5/4881; G16H 40/60; G16H 40/67; G16H 40/63
See application file for complete search history.

(56) References Cited

U.S. PATENT DOCUMENTS

| | | |
|---|---|---|
| 8,326,546 B2 | 12/2012 | Stewart et al. |
| 8,352,196 B2 | 1/2013 | Vering et al. |
| 9,498,165 B2 | 11/2016 | Johnson et al. |
| 10,771,607 B2 | 9/2020 | Mandapaka et al. |

(Continued)

FOREIGN PATENT DOCUMENTS

| | | |
|---|---|---|
| EP | 1972270 | 11/2010 |
| EP | 2006786 | 5/2018 |
| WO | 2018125841 | 5/2018 |

OTHER PUBLICATIONS

International Search Report & Written Opinion dated Jan. 25, 2021 for International Patent Application No. PCT/US20/48851.

*Primary Examiner* — Allen Porter
*Assistant Examiner* — Avery M Foley
(74) *Attorney, Agent, or Firm* — Morris, Manning & Martin, LLP; Bryan D. Stewart

(57) ABSTRACT

Glucose exposure can be indicative of a number of potential underlying health conditions. The present disclosure is directed to measuring glucose exposure, determined, for example, on an hourly basis. This glucose exposure, in at least one embodiment, represents a current glucose level over the span of given period (e.g., a portion of 24 hours). If a patient's glucose exposure exceeds a glucose threshold or limit (for a 24 hour period in some embodiments), then a variety of treatments may be administered to the patient to help lower overall glucose exposure (e.g., during the 24 hour period).

20 Claims, 7 Drawing Sheets

(56) References Cited

U.S. PATENT DOCUMENTS

| | | |
|---|---|---|
| 10,867,420 B2 | 12/2020 | Zamanakos et al. |
| 11,020,027 B2 | 6/2021 | Park et al. |
| 2003/0217966 A1 | 11/2003 | Tapsak et al. |
| 2006/0189863 A1 | 8/2006 | Peyser et al. |
| 2007/0083335 A1* | 4/2007 | Moerman ............ A61B 5/7275 702/19 |
| 2010/0298685 A1* | 11/2010 | Hayter ................ A61M 5/142 600/365 |
| 2011/0245634 A1* | 10/2011 | Ray .................... A61B 5/14532 600/309 |
| 2013/0096842 A1 | 4/2013 | Sato et al. |
| 2014/0005499 A1 | 1/2014 | Catt et al. |
| 2014/0088393 A1 | 3/2014 | Bernstein et al. |
| 2014/0200426 A1* | 7/2014 | Taub ................ A61B 5/14532 600/347 |
| 2014/0313052 A1* | 10/2014 | Yarger .................. G08C 17/02 340/870.02 |
| 2017/0071511 A1 | 3/2017 | Garcia et al. |
| 2018/0235524 A1 | 8/2018 | Dunn et al. |
| 2018/0256103 A1 | 9/2018 | Cole et al. |
| 2019/0320976 A1* | 10/2019 | Roslin .................... G16H 40/63 |
| 2019/0348164 A1* | 11/2019 | Bengtsson .......... A61M 5/1723 |
| 2020/0164209 A1* | 5/2020 | Hogg ................ A61N 1/36014 |
| 2020/0196865 A1 | 6/2020 | Kamath et al. |
| 2020/0203012 A1 | 6/2020 | Kamath et al. |
| 2020/0272319 A1 | 8/2020 | Bhavaraju et al. |

* cited by examiner

GLUCOSE EXPOSURE DIAGNOSTICS AND THERAPEUTICS RELATED THERETO

BACKGROUND

Average glucose monitoring is typically measured on a 24 hour basis and over time (e.g., what is a person's average 24 hour glucose, averaged over weeks or months). This average glucose data may be used to determine a number of factors. Such factors include, but are not limited to, diabetes, pre-diabetes, insulin resistance, etc. While controlling/understanding average 24 hour glucose (averaged over time), more granular glucose monitoring may help control glucose throughout a day and may lead to administration of therapeutics/treatments, which may help prevent or control (or better control) glucose-related ailments and issues.

Thus, there is a long-felt but unresolved need for a system or process that continuously monitors and reports glucose levels in the context of overall glucose targets or limits, which may provide a diagnostic of particular ailments and lead to administration of treatment options based on the glucose levels.

BRIEF SUMMARY OF THE DISCLOSURE

Briefly described, and according to one embodiment, aspects of the present disclosure generally relate to systems and processes for measuring glucose exposure, diagnosing glucose over exposure, and treatments for the same.

The present disclosure generally relates to diagnostics and treatments based on measured glucose exposure, determined, for example, on an hourly basis. The treatments may include, but is not limited to prescribing, recommending and/or administering to the user insulin, medications for the treatment of Nonalcoholic Fatty Liver Disease and/or Nonalcoholic Steatohepatitis, including insulin-sensitizing drugs, vitamin E, and/or exercise and low-carbohydrate diet, medication for pre-diabetic users, weight loss medication. This glucose exposure, in at least one embodiment, represents a current glucose level of a user over the span of given period (e.g., a portion of 24 hours).

For example, the present systems and processes may determine (or receive) a 24 hour glucose target or limit and determine a glucose limit or target for a particular hour (e.g., at 10:00 AM, a user should have a glucose exposure of 1000 mg/dl, where 1000 mg/dl is a summation of glucose from previous hours in the day). Continuing with this example, the present systems and methods may determine a glucose exposure for the user of 1010 mg/dl by summing the glucose exposure of the user for each hour until 10:00 AM. The present systems and methods, in this example, may display the current glucose exposure (e.g., 1010 mg/dl) as a percentage or comparison of the glucose target or limit of 1000 mg/dl, potentially indicating that the user to trending towards a glucose level that is over the glucose target or limit for the 24 hour period. In certain situations, for example, if the current glucose exposure is higher than the glucose target or limit by a certain percentage, the system may administer a treatment to the user to decrease the current glucose exposure.

According to a first aspect, a method for treating glucose over exposure may include receiving indications of glucose levels of a patient via a filament interacting with interstitial fluid on a particular interval, determining an average glucose level for a particular hour by averaging one or more indications of the glucose levels of the patient received during the particular hour, determining a current glucose exposure for the particular hour by adding the average glucose level for the particular hour to a summation of average glucose levels of the patient for hours preceding the particular hour in a 24-hour period, determining a target glucose level for the particular hour by multiplying a glucose exposure limit per hour by the numerical expression of the particular hour, and if the current glucose exposure for the particular hour exceeds the target glucose level for the particular hour, administering treatment to the patient to lower the patient's glucose exposure level to at or below a 24-hour glucose exposure limit before the end of the 24-hour period.

According to a second aspect, the method for treating glucose over exposure of the first aspect or any other aspect, wherein the treatment includes insulin.

According to a third aspect, the method for treating glucose over exposure of the second aspect or any other aspect, wherein the treatment includes one or more of the group including rapid-acting insulin, short-acting insulin, intermediate-acting insulin, mixed-insulin, or long-acting insulin.

According to a fourth aspect, the method for treating glucose over exposure of the first aspect or any other aspect, wherein the treatment includes pioglitazone. According to a fifth aspect, the method for treating glucose over exposure of the first aspect or any other aspect, wherein the treatment includes one or more weight loss drugs.

According to a sixth aspect, the method for treating glucose over exposure of the first aspect or any other aspect, wherein the treatment includes one or more drugs to treat nonalcoholic fatty liver disease or nonalcoholic steatohepatitis.

According to a seventh aspect, the method for treating glucose over exposure of the first aspect or any other aspect, wherein the glucose limit per hour is based at least in part on historical glucose exposure data for the patient.

According to an eighth aspect, the method for treating glucose over exposure of the first aspect or any other aspect, wherein the particular interval is 15 minutes.

According to a ninth aspect, the method for treating glucose over exposure of the eighth aspect or any other aspect, wherein determining the average glucose level for the particular hour includes averaging four indications of the current glucose level of the patient received during the particular hour.

According to a tenth aspect, the method for treating glucose over exposure of the first aspect or any other aspect, wherein the particular interval is 1 minute.

According to a eleventh aspect, the method for treating glucose over exposure of the tenth aspect or any other aspect, wherein determining the average glucose level for the particular hour includes averaging 60 indications of the current glucose level of the patient received during the particular hour.

According to a twelfth aspect, the method for treating glucose over exposure of the first aspect or any other aspect, wherein the 24-hour glucose exposure limit includes a summation of the glucose limit per hour for 24 hours.

According to a thirteenth aspect, the method for treating glucose over exposure of the twelfth aspect or any other aspect, wherein the average glucose levels of the patient for hours preceding the particular hour in the 24-hour period includes at least one average glucose level based on historical data.

According to a fourteenth aspect, the method for treating glucose over exposure of the thirteenth aspect or any other aspect, wherein the at least one average glucose level includes an average of average glucose levels for an hour immediately preceding the particular hour and an hour immediately succeeding the particular hour in a different 24-hour period.

According to a fifteenth aspect, the method for treating glucose over exposure of the thirteenth aspect or any other aspect, wherein the at least one average glucose level includes an average of stored glucose exposure data for the particular hour for different 24-hour periods.

According to a sixteenth aspect, the method of diagnosing and treating glucose over exposure may include receiving a current glucose exposure for a particular hour, wherein the current glucose exposure for the particular hour is determined by adding an average glucose level for the particular hour to a summation of average glucose levels of a patient for hours preceding the particular hour in a 24-hour period, wherein: A) the average glucose level for the particular hour is determined by averaging one or more indications of a glucose level of the patient received during the particular hour; and B) the one or more indications of the current glucose level of the patient are derived from a filament interacting with interstitial fluid, determining a target glucose level for the particular hour based on a glucose exposure limit, and if the current glucose exposure for the particular hour exceeds the target glucose level for the particular hour, administering treatment to the patient to lower the patient's glucose exposure level to at or below the glucose exposure limit.

According to a seventeenth aspect, the method of diagnosing and treating glucose over exposure of the sixteenth aspect or any other aspect, wherein the glucose exposure limit is a 24-hour glucose exposure limit.

According to a eighteenth aspect, the method of diagnosing and treating glucose over exposure of the sixteenth aspect or any other aspect, wherein the glucose exposure limit is a glucose exposure limit for less than 24 hours.

According to a nineteenth aspect, the method for treating glucose over exposure of the first aspect or any other aspect, wherein the treatment includes one or more of the group including rapid-acting insulin, short-acting insulin, intermediate-acting insulin, mixed-insulin, or long-acting insulin.

According to a twentieth aspect, the method for treating glucose over exposure of the first aspect or any other aspect, wherein the treatment includes one or more drugs to treat nonalcoholic fatty liver disease or nonalcoholic steatohepatitis.

According to a twenty-first aspect, the method for treating diabetes or pre-diabetes may include the steps of receiving indications of a current glucose level of a patient via a filament interacting with interstitial fluid at one or more intervals, determining an average glucose level for a particular hour by averaging one or more indications of the current glucose level of the patient over the one or more intervals received during the particular hour, determining a current glucose exposure for the particular hour by adding the average glucose level for the particular hour to a summation of average glucose levels of the patient for hours preceding the particular hour in a 24-hour period, determining a target glucose level for the particular hour based on a glucose exposure limit, and if the current glucose exposure for the particular hour exceeds the target glucose level for the particular hour, administering insulin to the patient to lower the patient's glucose exposure level.

These and other aspects, features, and advantages of the claimed invention(s) will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE FIGURES

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein.

DETAILED DESCRIPTION

Figure 1:
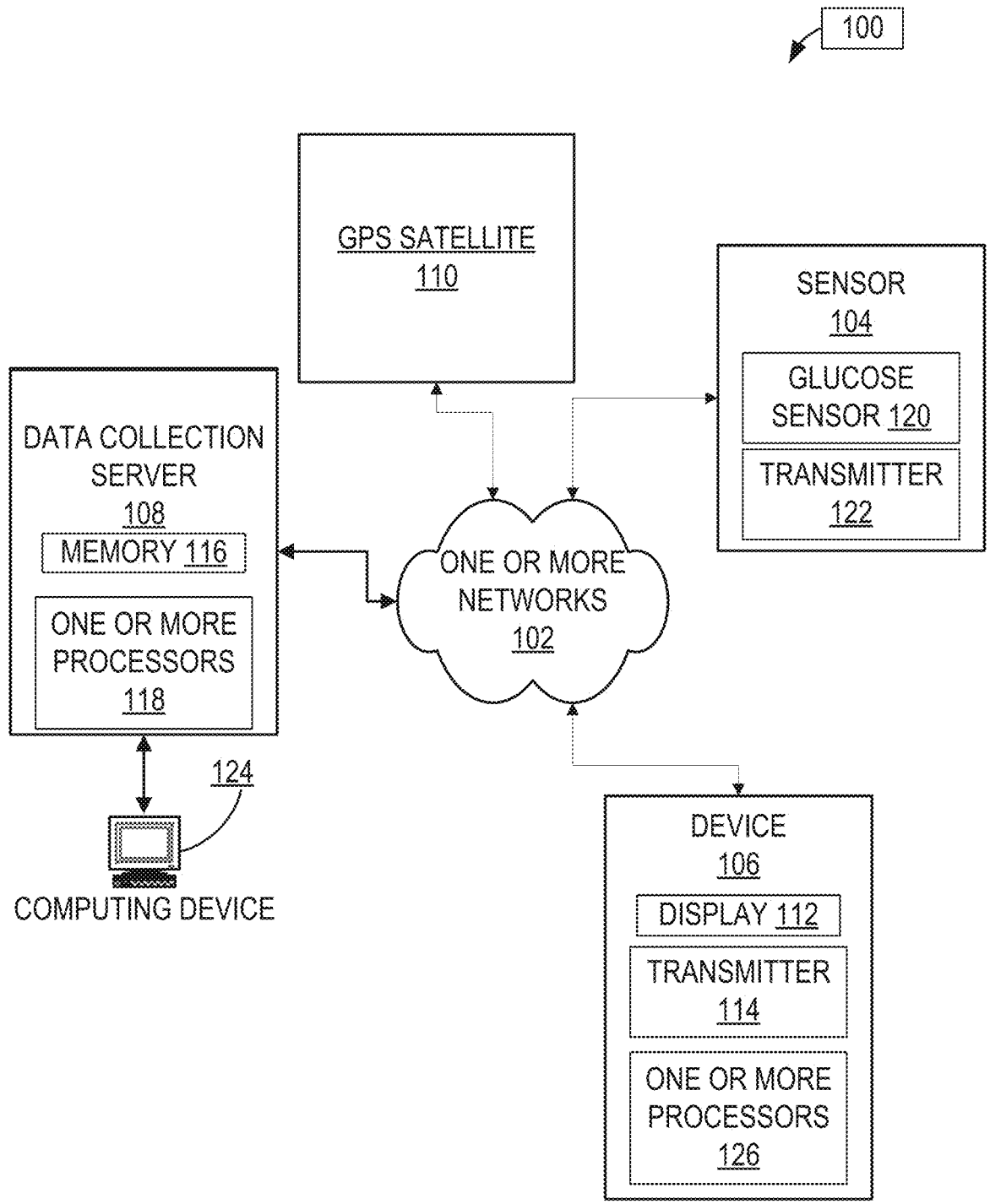
FIG. 1 is a diagram of an exemplary glucose exposure system, according to one embodiment of the present disclosure.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Overview

In various embodiments, the present systems and processes determine glucose exposure for a particular patient (also "user") on an hourly basis. The present systems and processes may, in at least one embodiment, thereby diagnose when the particular patient is over glucose exposed and administer or recommend administration of therapeutic treatments based on the determined glucose exposure. The therapeutic treatments may treat diseases such as but not limited to obesity, diabetes, nonalcoholic fatty liver disease, nonalcoholic steatohepatitis, and pre-diabetic conversion to type-II diabetes. Treatments include, but are not limited to prescribing, recommending and/or administering to a patient insulin, medications for the treatment of Nonalcoholic Fatty Liver Disease and/or Nonalcoholic Steatohepatitis, exercise, low-carbohydrate meals or diets, medication for pre-diabetic users, and/or weight loss medication. The treatments may be based on the patient's current glucose exposure as compared to a target glucose level for a particular hour, such that, if the patient's current glucose exposure exceeds the target glucose level for the particular hour, the patient may be administered treatment.

To determine the glucose exposure, in at least one embodiment, the systems and processes determine average glucose level for the patient for each hour, then sum the average glucose level per hour over the number of hours currently passed in a given day to determine a glucose exposure for the current time/hour (e.g., sums the average glucose from 12:00 AM-1:00 AM, 1:00 AM-2:00 AM, 2:00 AM-3:00 AM, and 4:00 AM-5:00 AM to determine a glucose exposure at 5:00 AM).

In order to determine an average glucose level for an hour, in at least one embodiment, the disclosed systems and processes: a) receive glucose data (e.g., an indication of current glucose levels of a user) from a sensor in predetermine intervals (e.g., 15 minutes); and b) averages the received glucose data over an hour (e.g., averages four glucose indication taken at 15 minute intervals over the hour).

In at least one embodiment, the present systems and processes display current glucose exposure for a particular hour as a percentage of a glucose target or limit for the day and/or hour (or a limit/target for a day thus far). In some embodiments, the systems and processes may create alerts based on current glucose exposure. For example, if a user's current glucose exposure is over the target or limit for the hour (e.g., thus far in the day), then the systems and processes may recommend that the user embark on glucose reducing or limiting actions (e.g., go for a walk, eat a low carb lunch, etc.). In this way, the systems and processes may enable a user to tweak habits or actions to influence glucose exposure during a day.

In at least one embodiment, the systems and processes may "backfill" glucose data for times when a sensor (e.g., that reads a user's glucose) is disconnected or glucose indications or readings are otherwise unavailable (e.g., data could be corrupted, unavailable, or otherwise unusable) via one or more processes or mechanisms discussed herein.

For example, in one embodiment, a user (or the system) may set a target glucose limit of 1200 units of measurement (such as, e.g., milligrams per deciliter) per day. Based on the target glucose limit, the glucose exposure system may determine at a given time the target glucose limit for that given time, as well as the user's glucose exposure. Continuing with the above example, if the day begins at midnight (00:00 AM) and goes for 24 hours, then the glucose exposure limit per hour would be 50 mg/dl. If the user checks his glucose exposure at 8:00 AM, the target glucose exposure would be 400 milligrams, and the glucose exposure system would display the user's glucose exposure (e.g., 390 mg/dl based on sensor indications, as discussed herein) compared to the target glucose for 8:00 AM, to indicate to the user if the user was below, at, or above the target glucose exposure limit for 8:00 AM.

Exemplary Embodiments

Referring now to the figures, for the purposes of example and explanation of the fundamental processes and components of the disclosed systems and methods, reference is made to FIG. 1, which illustrates an exemplary system diagram 100 of one embodiment of a glucose exposure system. As will be understood and appreciated, the exemplary diagram 100 shown in FIG. 1 represents merely one approach or embodiment of the present system, and other aspects are used according to various embodiments of the present system.

As shown in FIG. 1, according to one embodiment, the system 100 may include one or more networks 102, a sensor 104, a device 106, a data collection server 108, and a GPS satellite 110.

In various embodiments, the sensor 104 may include a glucose sensor 120 and a transmitter 122. In one or more embodiments, the glucose sensor 120 may be a filament that interacts with a user to derive glucose data. In some embodiments, the glucose data/information may include an indication of a glucose level of a patient, such as, but not limited to, an electronic signal. In at least one embodiment, the glucose sensor 120 may interact with interstitial fluid or other bodily fluid of the user to derive the glucose data. In several embodiments, the glucose sensor 120 may interact with the interstitial fluid or other bodily fluid of the user at a particular interval.

In multiple embodiments, the sensor 104 may also include a transmitter 122. In many embodiments, the transmitter 122 may transmit the derived glucose data from the sensor 104 to the data collection server 108 or device 106, via the one or more networks 102. In at least one embodiment, the transmitter 122 may transmit via Bluetooth radio, near-field communication (NFC), and other similar wireless communication tools.

In various embodiments, the sensor 104 receives an electronic signal from the glucose sensor 120 that indicates the amount of glucose in the interstitial fluid. In many embodiments, the sensor 104 measures the electronic signal (e.g., voltage change or the like) from the glucose sensor 120, and, from that measurement, the sensor 104 determines how much glucose is present, which the sensor 104 reads as glucose data. In one embodiment, the glucose data may include an amount of glucose in the user's interstitial fluid. In many embodiments, the amount of glucose may be measured in a unit of measurement (e.g., milligrams per deciliter). In one or more embodiments, the sensor 104 obfuscates the glucose data before transmitting the obfuscated glucose data, via the transmitter 122, to the device 106 or data communication server 108. In at least one embodiment, the sensor 104 may obfuscate the glucose data by encryption, one or more hashing algorithms, or other similar processes.

In at least one embodiment, the sensor 104 may receive an electronic signal from the glucose sensor 120 that indicates the amount of glucose in the interstitial fluid of the user. In some embodiments, the sensor 104 may measure the electronic signal, but may not translate the electronic signal into a corresponding amount of glucose present. In one or more embodiments, the sensor 104 instead may obfuscate the raw electronic signal data by encryption, one or more hashing algorithms, or other similar processes, and transmit the raw electronic signal data to the device 106 for translation into corresponding milligrams per deciliter. In many embodiments, the device 106 may deobfuscate the electronic signal data, or transmit the obfuscated electronic signal data to the data connection server 108 to be deobfuscated. In some embodiments, once the electronic signal data is deobfuscated, the device 106 or data connection server 108 may read the electronic signal data and determine, from the electronic signal data, the amount of glucose in the user's interstitial fluid (in milligrams per deciliter).

In a further embodiment, the sensor 104 may also create a timestamp when receiving the electronic signal from the glucose sensor 120, and may associate the timestamp with the received electronic signal or measured voltage change (or other electronic data). In multiple embodiments, the timestamp data may be included in the glucose data that is obfuscated and transmitted to the device 106. In one or more embodiments, the sensor 104 may associate an identifier with the received electronic signal from the glucose sensor 120. In at least one embodiment, the sensor 104 may include the identifier in the glucose data, and obfuscate and transmit the identifier, along with the glucose data, to the device 106.

In several embodiments, the device 106 may be a mobile device, tablet, smart watch, laptop, web application, or similar devices. In one or more embodiments, the device 106 may be wearable by the user. In at least one embodiment, the device 106 may include a display 112, a transmitter 114, and one or more processors 126. In many embodiments, the display 112 may display the user's glucose exposure data, target glucose exposure data, a comparison between the user's glucose exposure data and target glucose exposure data, and/or other data related thereto.

In multiple embodiments, the device 106 may receive, via one or more radios, the glucose data, obfuscated or deobfuscated, from the sensor 104 or the data collection server 108, via the one or more networks 102. In at least one embodiment, the transmitter 114 may transmit via Bluetooth radio, NFC, and other similar wireless communication tools. In many embodiments, one or more radios on the device 106 may receive from the sensor 104 or data communication server 108 via Bluetooth radio, NFC, and other similar wireless communication tools. In various embodiments, the data collection server 108 may include memory 116 and one or more processors 118. In at least one embodiment, the memory 116 may include a storage database. In some embodiments, the memory 116 may store historical deobfuscated glucose data, along with associated time stamps, identifiers, and other associated data, for the user. In some embodiments, the data collection server 108 may retrieve the historical deobfuscated glucose data from the memory 116 for determining missing glucose exposure data.

In many embodiments, the data collection server 108 may be operatively connected to a computing device 124.

In one or more embodiments, the data collection server 108 and/or device 106 may receive the obfuscated glucose data from the sensor 104. In several embodiments, the data collection server 108 and/or device 106 may receive the obfuscated glucose data from the sensor 104 at a particular interval. In at least one embodiment, the particular interval may be a range of time from one second to one hour. For example, the data collection server 108 and/or device 106 may receive obfuscated glucose data from the sensor 104 every second, or may receive the obfuscated glucose data from the sensor once per hour, or any other interval therebetween.

In multiple embodiments, the sensor 104 may collect glucose data from the glucose sensor 120 over a predetermined interval, but, instead of transmitting each glucose data upon receiving the electronic signal from the glucose sensor 120, the sensor 104 may store the glucose data and batch the glucose data for transmitting. In many embodiments, the sensor 104 may transmit a batch of glucose data to the device 106 or data collection server 108 after a specific amount of time or after a specific amount of glucose data has been received from the glucose sensor 120. For example, in this embodiment, the glucose sensor 120 may send the sensor 104 the glucose data at a constant rate (e.g., one per second), but the sensor 104 may collect multiple glucose data from the glucose sensor 120 and only transmit the glucose data to the device 106 or data collection server 108 once the sensor 104 has received a specific amount of glucose data (e.g., every five, ten, or twenty glucose data) from the glucose sensor 120 (e.g., in a batch). In one embodiment, the predetermined interval may be the amount of time between the glucose sensor 120 sending indications to the sensor 104.

In many embodiments, the data collection server 108 and/or device 106 may store the obfuscated glucose data in the memory 116. In several embodiments, the device 106, utilizing the one or more processors 126, and/or the data collection server 108, utilizing the one or more processors 118, may deobfuscate the obfuscated glucose data. In one or more embodiments, once the obfuscated glucose data is deobfuscated, the (deobfuscated) glucose data may be stored in the memory 116 and/or in the device 106 (as will be understood, the device 106 may include local memory/storage). In at least one embodiment, the glucose data may be stored in the memory 116 and/or the device 106 for a certain amount of time, including, but not limited to, ninety days.

In various embodiments, the system 100 may also include a GPS satellite 110. In one or more embodiments, the GPS satellite 110 may be utilized to track the location of the device 106. In many embodiments, the system 100 may utilize the location of the device 106 as movement data for the user, and calculate a distance traveled by the user based on changing locations of the device 106. In at least one embodiment, the glucose disclosure system may also calculate the speed of the user by dividing the distance traveled by the user by the time it took for the user to travel the distance.

According to particular embodiments, the device 106 may include any suitable additional components, such as, but not limited to, a gyroscope, accelerometer, heart rate sensor, pulse oximeter, etc. In one embodiment, the device 106 and/or data collection service 108 may determine a step count or other suitable data for a user wearing the device 106.

Figure 2A:
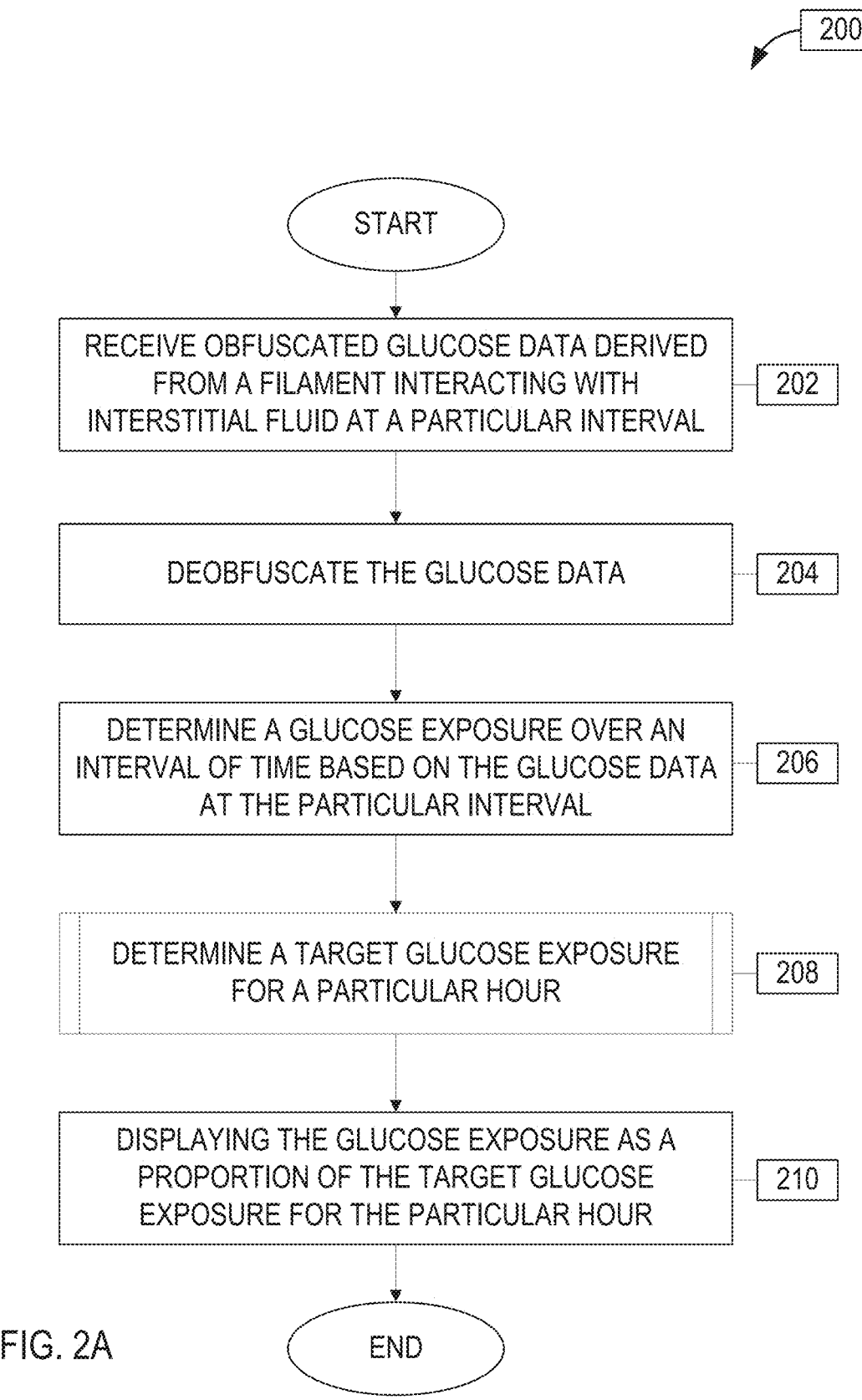
FIG. 2A is a flow chart of an exemplary glucose exposure process, according to one embodiment of the present disclosure.

As shown in FIG. 2A, an exemplary glucose exposure process 200 is described, according to one embodiment of the present disclosure. In various embodiments, a user may first connect the sensor 104 to the user's body, such that the glucose sensor 120 is interacting with the interstitial fluid or otherwise determining a level of glucose within the patient's blood.

According to one embodiment, at step 202 of process 200, the system 100 may receive the obfuscated glucose data from the transmitter 122 of the sensor 104 at a particular interval. In at least one embodiment, the obfuscated glucose data is derived from the glucose sensor 120 interacting with the user, and specifically, with the user's interstitial fluid. In one or more embodiments, the system 100 may receive the obfuscated glucose data at the device 106 or the data collection server 108.

In multiple embodiments, the particular interval is a time interval by which the system 100 receives the obfuscated glucose data from the sensor 104. In many embodiments, the particular interval may one second, or may be one day, or any time therebetween. For example, in one embodiment, the particular interval may be 15 minutes, 30 minutes, 1 hour, 1 day, etc.

In several embodiments, the particular interval may be the time interval between the glucose sensor 120 transmitting indications to the sensor 104. In this embodiment, when the sensor 104 receives an indication of glucose data from the glucose sensor 120, the sensor 104 may also record a timestamp and associate the time stamp with the received glucose data. Continuing in this embodiment, the sensor 104 may thereafter transmit the glucose data and associated time stamp to the device 106 and/or data connection server 108.

At step 204, in various embodiments, the system 100 may deobfuscate the obfuscated glucose data received from the sensor 104. In one or more embodiments, the device 106 or the data collection server 108 may deobfuscate the obfuscated glucose data. As will be understood from discussions here, the sensor 104 may obfuscate glucose data via encryption, hashing, steganography, etc. In some embodiments, once the device 106 receives the obfuscated (or encrypted) glucose, the device 106 may deobfuscate, decrypt, or otherwise decode the glucose data. In at least one embodiment, the device 106 may transmit the obfuscated to the data collection server 108 for deobfuscation.

At step 206, in multiple embodiments, the system 100 may determine a glucose exposure over an interval of time based on the glucose data at the particular time interval. In several embodiments, the glucose exposure over the interval of time may be an average of the received glucose data at the particular interval over the course of the interval of time. In one or more embodiments, the interval of time may be the same amount of time as the particular interval, or may be a longer amount of time such that the glucose exposure may be based on more data. In at least one embodiment, the interval of time may be fifteen, thirty, or sixty minutes, a number of hours (see example below regarding a running total), or some other amount of time. For example, in one embodiment, the particular interval may be fifteen minutes, and the interval of time may be sixty minutes, such that the system 100 receives glucose data four times within the interval of time. Continuing with this example, the received glucose data over the sixty minute interval of time may be 90, 92.5, 97.5, and 100 (in units of measurement), which averages to a glucose exposure of 95 units of measurement over the sixty minute interval of time.

In a further embodiment, the system 100 may calculate a running total of glucose exposure through a twenty-four hour day by adding the determined glucose exposures over the intervals of time (or a single interval of time might be the time of the running total) throughout the twenty-four hours in a day. For example, in one embodiment, if the interval of time is sixty minutes, and the twenty-four hour day begins at midnight (00:00 AM), the system 100 may add each glucose exposure over the interval of sixty minutes over the course of the twenty-four hour day, so that, at a particular hour (e.g., 9:00 AM), the system 100 may determine the total glucose exposure for the user for the day at 9:00 AM.

In an alternate embodiment, the system 100 may utilize a weighted average for determining the glucose exposure over the interval of time. In this alternate embodiment, the system 100 may give more weight to the glucose data received closer to the end of the interval of time and less weight to the glucose data received nearer to the beginning of the interval of time, so that the glucose exposure over the interval of time is closer to the current glucose exposure at the end of the interval of time. For example, in this alternate embodiment, if the system 100 received, in order, the glucose data at the particular interval of 90, 92.5, 97.5, and 100 (in units of measurement such as, e.g., in milligrams) over the interval of time, the weighted average may be greater than the actual average 95 of the glucose data.

As described in step 208, in various embodiments, the system 100 may determine a target glucose level for a particular hour. In one or more embodiments, and as shown in more detail in FIG. 2B, the target glucose level for the particular hour may be the amount of glucose exposure the user is trying to attain for the particular hour. As discussed in more detail below, in some embodiments, step 208 includes dividing a daily glucose exposure limit by 24 to get a glucose exposure limit per hour (step 212) and multiplying the glucose exposure limit per hour by a numerical expression of the particular hour (step 214). In some embodiments, the target glucose level for the particular hour may be a limit of glucose exposure that the user is trying not to exceed. In at least one embodiment, the particular hour may be a specific time during a twenty-four hour period. For example, in one embodiment, the particular hour may be 9:00 AM.

As described in step 210, in multiple embodiments, the system 100 may display the glucose exposure as a proportion of the target glucose level for the particular hour. In at least one embodiment, the system 100 may compare the running total of the glucose exposure for the user at the particular hour to the target glucose level for the particular hour. In an alternate embodiment, the system 100 may compare the glucose exposure over the interval of time to the glucose exposure limit per hour.

For example, in several embodiments, if the interval of time is sixty minutes, then the system 100 will determine the glucose exposure of the user every sixty minutes. Continuing with the example, in some embodiments, the running total of glucose exposure at a particular hour may be the sum of the determined glucose exposure data from the previous intervals of time for the day. Still continuing with this example, in many embodiments, if the interval of time is sixty minutes, the running total of glucose exposure at 10:00 AM may be the sum of the determined glucose exposures from 1:00 AM, 2:00 AM, 3:00 AM . . . 10:00 AM. Still continuing with this example, in one or more embodiments, if the previous determined glucose exposures for the day were 63 (00:00 AM), 60, 65, 73, 80, 84, 88, 90, 93, 95, and 97 (10:00 AM), then the running total of the glucose exposure at 10:00 AM is 888 units of measurement of glucose exposure. Continuing with this example, in one embodiment, if the target glucose exposure for 10:00 AM is 910 units of measurement of targeted glucose exposure, the system 100 may display 888 units of measurement of glucose exposure divided by 910 units of measurement of targeted glucose exposure. In a further embodiment, the system 100 may display the proportion of the glucose exposure to the target glucose exposure as a percentage.

In various embodiments, the system 100 may determine a 24-hour average glucose for the user. In many embodiments, the system may calculate the 24-hour average glucose by averaging the user's determined glucose exposure data from the previous 24-hour period. In some embodiments, the 24-hour average glucose may be a rolling average such that the 24-hour average glucose may be recalculated once an hour or once every interval of time in which the glucose exposure is determined. For example, in one embodiment, the 24-hour average glucose at 11:00 AM may be an average of the determined glucose exposure data for the previous 24 hours (e.g., from about 11:00 AM previous day to 11:00 AM current day), while the glucose exposure at the particular hour (11:00 AM) may be the sum of the glucose exposure data from midnight of the current day to 11:00 AM of the current day (eleven hours). In at least one embodiment, the system may display the 24-hour average glucose. In one or more embodiments, the system may compare the current 24-hour period to an immediately preceding 24-hour average glucose. In one embodiment, the system may display the difference between the current 24-hour average glucose to the immediately preceding 24-hour average glucose as a percentage. In some embodiments, system 100 may store the 24-hour average glucose determinations for previous days (e.g., the 24-hour average glucose determination from midnight (00:00 AM) to the next midnight (24:00) to be utilized in additional calculations.

In several embodiments, the system 100 may determine a seven-day average glucose for the user. In some embodiments, the system may calculate the seven-day average glucose by averaging the user's determined glucose exposure data from the previous seven-day period. In one or more embodiments, the system 100 may average the determined 24-hour average glucose for each of the preceding seven days to determine the seven-day average glucose. In at least one embodiment, the system 100 may display the seven-day average glucose. Similarly, in many embodiments, the system 100 may determine an average glucose for any time period (e.g., one month, one year), by averaging 24-hour average glucose determinations or seven-day average glucose determinations, or other similar glucose exposure calculations. In one embodiment, the system 100 may determine a median to calculate the 24-hour average glucose and/or seven-day average glucose.

Figure 2B:
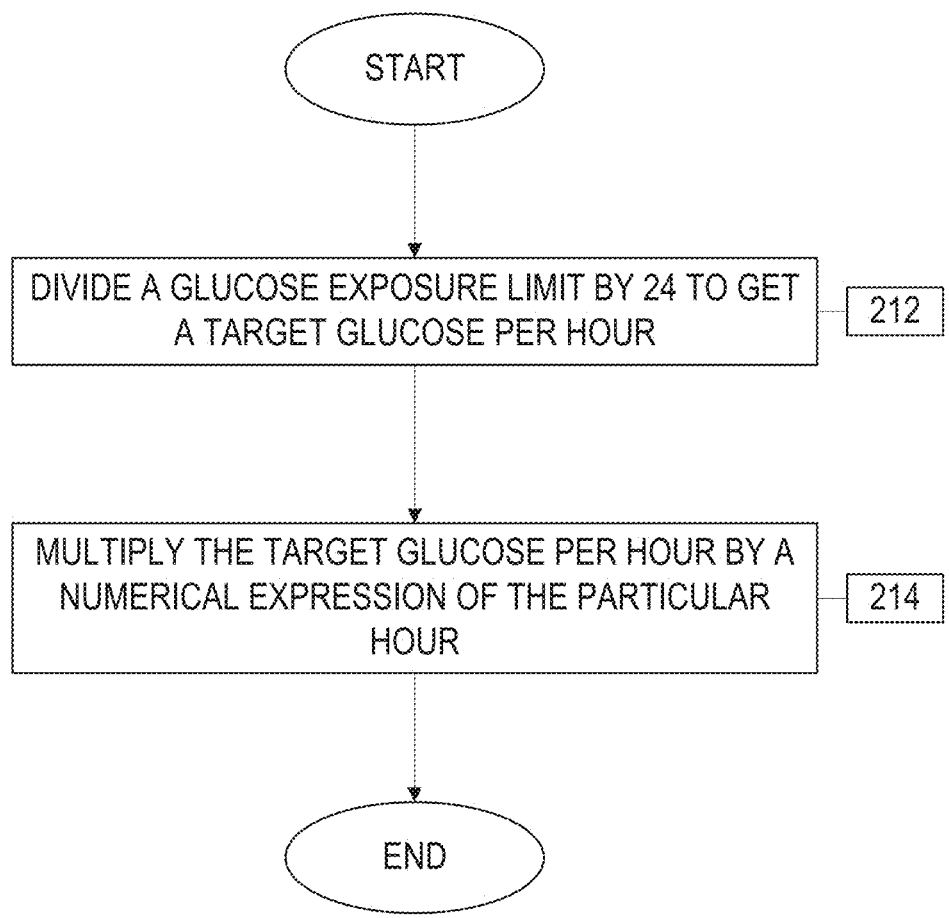
FIG. 2B is a flow chart of an exemplary target glucose level determination process, according to one embodiment of the present disclosure.

Turning now to FIG. 2B, an exemplary target glucose exposure determination process 208 is shown, according to one embodiment of the present disclosure. In multiple embodiments, in order to determine a target glucose level for a particular hour, the system 100 may first divide a glucose exposure limit by 24 to get a glucose exposure limit per hour. In one or more embodiments, the glucose exposure limit may be the maximum amount of glucose exposure the user desires over the course of a twenty-four hour day. In at least one embodiment, the user may input the glucose exposure limit into the system 100. For example, in one embodiment, the user may input a glucose exposure limit of 1200 units of measurement of glucose exposure into the system 100, which the system 100 divides by 24 to determine that the glucose exposure limit per hour is 50 units of measurement of glucose exposure.

In various embodiments, as shown in step 214, the system 100 may multiply the glucose exposure limit per hour by a numerical expression of the particular hour. In many embodiments, the numerical expression of the particular hour correlates to the particular time of day, using a 00:00-24:00 time measure for the time of day. For example, in one embodiment, the particular hour 11:00 AM correlates to 11 for the numerical expression of the particular hour. In a further embodiment, the minutes portion of the time of day correlates to a decimal for the numerical expression of the particular hour. For example, in the further embodiment, the time of day 5:15 PM correlates to 17.25 for the numerical expression of the particular hour.

According to one embodiment, as an example of steps 212 and 214, in multiple embodiments, the user may input a glucose exposure limit of 1800 units of measurement. In many embodiments, the system 100 may then divide the glucose exposure limit by 24, to get a glucose exposure limit per hour of 75 units of measurement per hour. Next, in several embodiments, if the particular hour is 3:00 PM, the system 100 may multiple the glucose exposure limit per hour by the numerical expression of 3:00 PM, which is 15. In one or more embodiments, the system 100 may determine that the target glucose exposure for 3:00 PM is 75 units of measurement per hour multiplied by 15 hours, which is 1125 units of measurement of glucose exposure.

In an alternative embodiment, the system 100 may divide the glucose exposure limit by 1440 to get a target glucose per minute. Continuing with this alternative embodiment, the system 100 may multiply the target glucose per minute by a numerical expression of a particular minute. In this alternative embodiment, the particular minute may be a specific minute during the day such that the numerical expression of the particular minute is between 0 and 1440. For example, still continuing in the alternative embodiment, at 1:45 PM, the particular minute is equal to thirteen hours multiplied by 60, and then added to the remaining 45 minutes, which is 825 minutes. In various embodiments, the system 100 may display the glucose exposure as a proportion to the target glucose exposure for the particular minute. In a further embodiment, similar calculations may be done so that the system 100 may determine a target glucose exposure for a particular second.

In a further embodiment, the glucose exposure limit may be a function of the user's personal information, such as, but not limited to, the user's height, weight, body mass index score, average daily exercise, average daily glucose exposure, whether the user is preparing for an endurance race, and/or other similar information. In this embodiment, the system 100 may calculate a healthy glucose exposure limit, based on algorithms and based on the user's personal health goals. For example, in one embodiment, the user may want to lose weight, so the user may input a "lose weight" goal into the system 100, and based on the user's personal information and other factors, the system 100 determines a glucose exposure limit for the user.

In a further embodiment, the system 100 may import or receive data from other devices that determine data about a user (or about other users). In various embodiments, the system 100 may store system 100 data in a server with other system 100 data for other users. In one or more embodiments, system 100 data may include the user's personal information, as well as the user's historical glucose data. In at least one embodiment, if a user updates the user's personal information and the update includes a change in body mass index score or weight, the system 100 may determine if the user has increased or decreased glucose exposure. In a further embodiment, the system 100 may deploy machine learning or AI to optimize the glucose exposure limits for a variety of user body types, by using measured glucose data against increases and decreases in users' weight and body mass index scores.

Figure 3A:
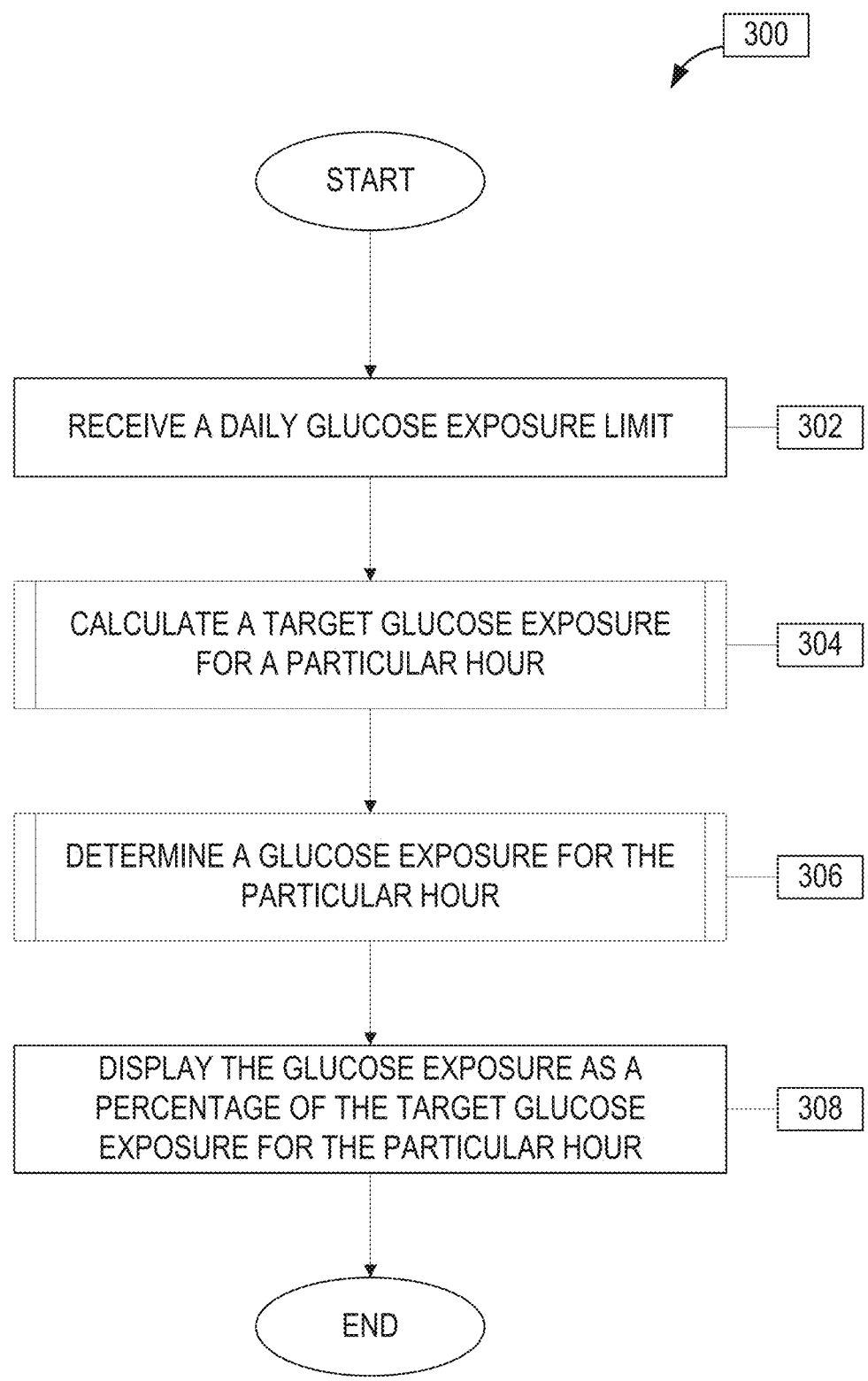
FIG. 3A is a flow chart of an exemplary glucose exposure process, according to one embodiment of the present disclosure.

In various embodiments, the system 100, at step 208, may receive, from the user or the system, a glucose exposure limit per hour. In several embodiments, the glucose exposure limit per hour may be utilized to calculate the target glucose level for a particular hour by multiplying the glucose exposure limit per hour by the numerical expression of the particular hour, as discussed infra. In one or more embodiments, the glucose exposure limit per hour may be multiplied by 24 to get a 24-hour glucose exposure limit. For example, in one embodiment, the user or the system may provide a glucose exposure limit per hour of 80 mg/dL, which the system may then multiply by 24 to determine the glucose exposure limit. Continuing with the example, in some embodiments, if the user checks his glucose exposure at 3:00 PM, and the 24-hour period began at midnight (00:00 AM), the system would multiply the glucose exposure limit per hour by 15 to get the target glucose level for the particular hour (1200 mg/dL). Still continuing with the above example, in many embodiments, the system may thereafter compare the user's glucose exposure with the target glucose level for the particular hour, and may also display the 24-hour glucose exposure limit. An exemplary glucose exposure process 300 is shown in FIG. 3A, according to one embodiment of the present disclosure. In various embodiments, a user may first connect the sensor 104 to the user's body, such that the glucose sensor 120 is interacting with the interstitial fluid or other bodily fluid.

As shown in step 302 of process 300, in multiple embodiments, the system 100 may receive a daily glucose exposure limit. In one or more embodiments, the user may input the daily glucose exposure limit into the system 100 via the device 106 or the computing device 124. In at least one embodiment, the daily glucose exposure limit may be the maximum amount of glucose exposure the user desires to receive over the course of a twenty-four hour day. In one or more embodiments, a medical professional or other third-party may input the daily glucose exposure limit into the system 100. In a further embodiment, a physician or other medical professional may prescribe a specific daily glucose exposure limit for the user. In some embodiments, the system 100 may calculate the glucose exposure limit based on weight loss goals, machine learning and artificial intelligence, physical activity goals, or other calculations.

At step 304, in various embodiments, the system 100 may calculate a target glucose level for a particular hour. As discussed in more detail below (in reference to FIG. 3B), in some embodiments, step 304 includes dividing a glucose exposure limit by 24 to get a glucose exposure limit per hour (step 310) and multiplying the glucose exposure limit per hour by a numerical expression of the particular hour (step 312). In one or more embodiments, the target glucose level for the particular hour may be the amount of glucose exposure the user is trying to attain for the particular hour. In many embodiments, the target glucose level for the particular hour may be a limit of glucose exposure that the user is trying not to exceed. In at least one embodiment, the particular hour may be a specific time during a twenty-four hour period. For example, in one embodiment, the particular hour may be 9:00 AM.

As shown in step 306, in several embodiments, the system 100 may determine a glucose exposure for the particular hour. As discussed in more detail below (in reference to FIG. 3C), in some embodiments, step 306 includes determining if a Bluetooth radio is connected to the sensor 104 (step 314), and if so, receiving, via the Bluetooth radio from the sensor 104, obfuscated glucose data (step 316), deobfuscating the data (step 318), and determining the glucose exposure over a time period based on the glucose data received at the predetermined interval (step 320), and if the Bluetooth radio is not connected to the sensor, determining an average glucose exposure for the particular hour based on historical data (step 322), and using the average glucose exposure for the particular hour as the glucose exposure for the particular hour (step 324).

At step 308, in many embodiments, the system 100 may display the glucose exposure calculated at step 306 as a percentage of the target glucose level for the particular hour calculated at step 304. For example, in one embodiment, the glucose exposure calculated at step 306 may be 1140 at the particular hour, and the target glucose level for the particular hour is 1080, which would be displayed as 105.5%.

Figure 3B:
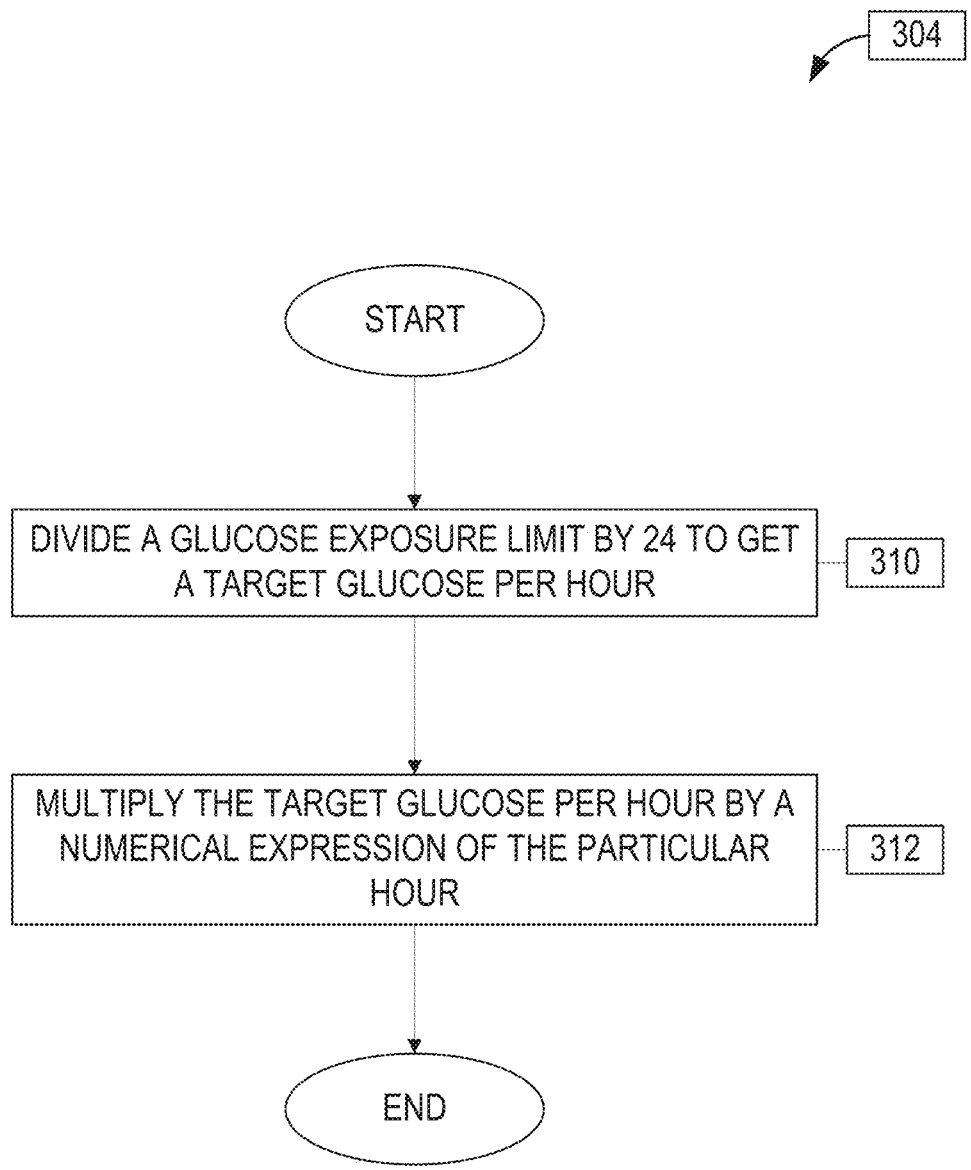
FIG. 3B is a flow chart of an exemplary target glucose level calculation process, according to one embodiment of the present disclosure.

As described in FIG. 3B, an exemplary target glucose exposure determination process 304 is shown, according to one embodiment of the present disclosure. As described in step 310, in multiple embodiments, in order to determine a target glucose level for a particular hour, the system 100 may first divide the daily glucose exposure limit by 24 to get a glucose exposure limit per hour. For example, in one embodiment, the user may input a glucose exposure limit of 1200 units of measurement of glucose exposure into the system 100, which the system 100 divides by 24 to determine that the glucose exposure limit per hour is 50 units of measurement of glucose exposure.

In various embodiments, as shown in step 312, the system 100 may multiply the glucose exposure limit per hour by a numerical expression of the particular hour. In many embodiments, the numerical expression of the particular hour correlates to the particular time of day, using a 00:00-24:00 time measure for the time of day. For example, in one embodiment, the particular hour 11:00 AM correlates to 11 for the numerical expression of the particular hour. In a further embodiment, the minutes portion of the time of day correlates to a decimal for the numerical expression of the particular hour. For example, in the further embodiment, the time of day 5:15 PM correlates to 17.25 for the numerical expression of the particular hour.

According to one embodiment, as an example of steps 310 and 312, in multiple embodiments, the user may input a glucose exposure limit of 1800 units of measurement. In many embodiments, the system 100 may then divide the glucose exposure limit by 24, to get a glucose exposure limit per hour of 75 units of measurement per hour. Next, in several embodiments, if the particular hour is 3:00 PM, the system 100 may multiple the glucose exposure limit per hour by the numerical expression of 3:00 PM, which is 15. In one or more embodiments, the system 100 may determine that the target glucose exposure for 3:00 PM is 75 units of measurement per hour multiplied by 15 hours, which is 1125 units of measurement of glucose exposure.

In various embodiments, the system 100, at step 304, may receive, from the user or the system, a glucose exposure limit per hour. In several embodiments, the glucose exposure limit per hour may be utilized to calculate the target glucose level for a particular hour by multiplying the glucose exposure limit per hour by the numerical expression of the particular hour, as discussed infra. In one or more embodiments, the glucose exposure limit per hour may be multiplied by 24 to get a 24-hour glucose exposure limit. For example, in one embodiment, the user or the system may provide a glucose exposure limit per hour of 80 mg/dL, which the system may then multiply by 24 to determine the glucose exposure limit. Continuing with the example, in some embodiments, if the user checks his glucose exposure at 3:00 PM, and the 24-hour period began at midnight (00:00 AM), the system would multiply the glucose exposure limit per hour by 15 to get the target glucose level for the particular hour (1200 mg/dL). Still continuing with the above example, in many embodiments, the system may thereafter compare the user's glucose exposure with the target glucose level for the particular hour, and may also display the 24-hour glucose exposure limit.

Figure 3C:
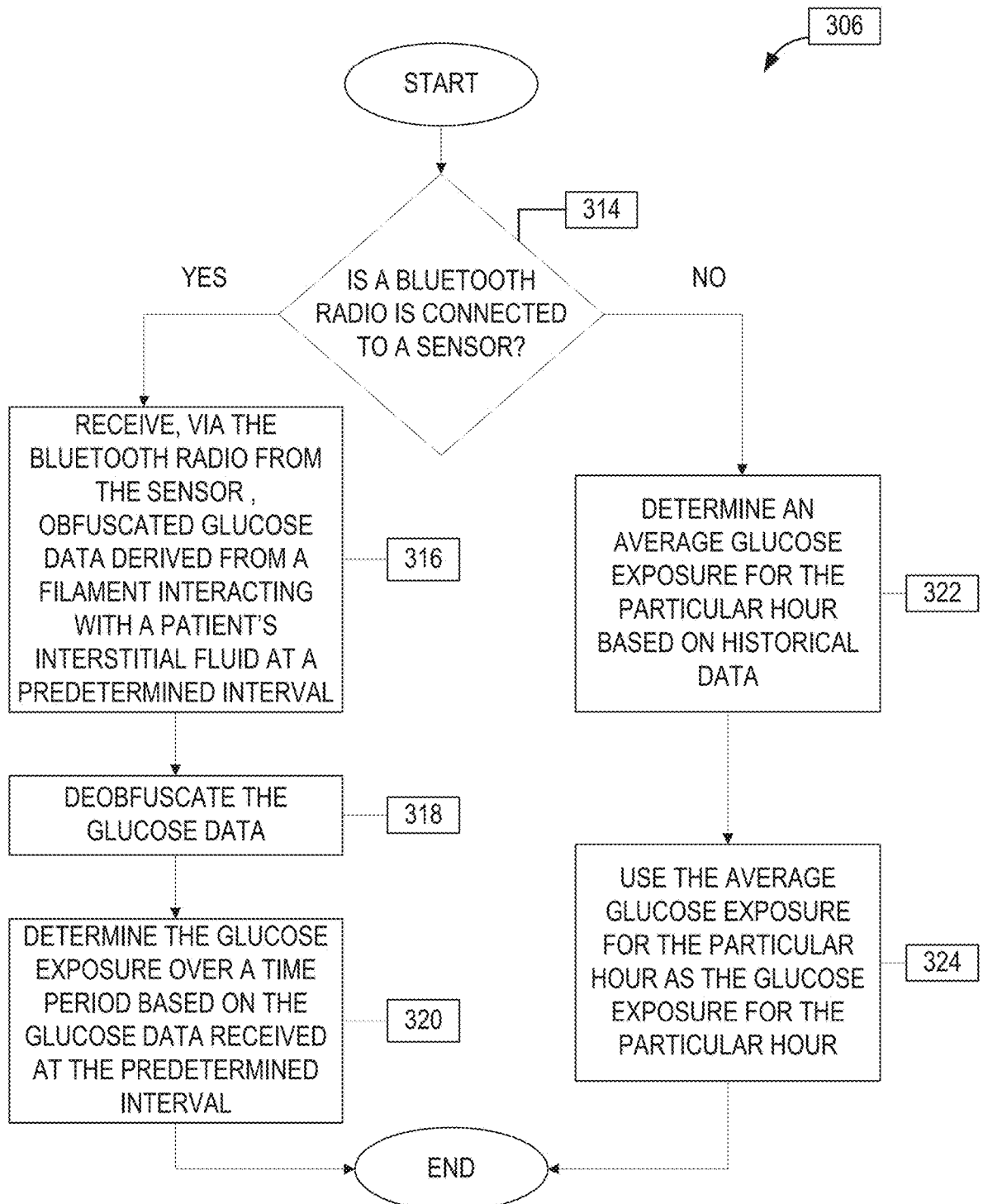
FIG. 3C is a flow chart of an exemplary glucose exposure for a particular hour determination process, according to one embodiment of the present disclosure.

FIG. 3C shows an exemplary glucose exposure for a particular hour determination process 306, according to one embodiment of the present disclosure. In various embodiments, at step 314 of process 306, the system 100 determines whether a Bluetooth radio is connected to the sensor 104. In one or more embodiments, the system 100 is wirelessly connected to the sensor 104.

In multiple embodiments, as shown in step 316, if a Bluetooth radio is connected to the sensor 104, then the system 100 receives, via the Bluetooth radio from the sensor 104, obfuscated glucose data derived from the glucose sensor 120 interacting with a patient's interstitial fluid at a predetermined interval. In one or more embodiments, the predetermined interval may be the time between the system 100 receiving glucose data from the sensor 104. In at least one embodiment, the predetermined interval may be one second, such that the system 100 is essentially constantly receiving obfuscated glucose data. In some embodiments, the predetermined interval may be one hour, such that the system 100 receives obfuscated glucose data once per hour. In many embodiments, the predetermined interval may be one day or multiple days.

In an embodiment, the sensor 104 may transmit a batch of indications/readings from the glucose sensor 120 to the system 100 instead of transmitting each individual indication upon receiving the indication from the glucose sensor 120. For example, in this embodiment, the glucose sensor 120 may send the sensor 104 the glucose data, as described above, at a constant rate (e.g., one indication per second), but the sensor 104 may collect a certain amount of glucose data from multiple indications (a batch) from the glucose sensor 120 (e.g., every five, ten, twenty indications) before transmitting the batch of glucose data to the system 100. In some embodiments, the batch may include an amount of indications from the glucose sensor 120 to the sensor 104 over a period of time (e.g., amount of indications per hour). Still continuing with this embodiment, the predetermined interval may be the amount of time between the glucose sensor 120 sending indications to the sensor 104 or may be the amount of time between the sensor 104 sending batches of indications to the system 100.

As described in step 318, in various embodiments, the system 100 deobfuscates the glucose data. In one or more embodiments, the device 106, the data collection server 108, or the computing device 124 may deobfuscate the glucose data. In some embodiments, the device 106 may receive the obfuscated glucose data via Bluetooth radio or other similar communication device. In at least one embodiment, the device 106, after receiving the obfuscated glucose data, may deobfuscate the glucose data or send the obfuscated glucose data to the data collection server 108, which will deobfuscate the glucose data. In one embodiment, if the device 106 sends the obfuscated glucose data to the data collection server 108, the data collection server 108 (or the connected computing device 124) may deobfuscate the glucose data, and the data collection server 108 may thereafter transmit the deobfuscated glucose data to the device 106. In many embodiments, once the glucose data is deobfuscated, the system 100 may read and utilize the glucose data.

As shown in step 320, in several embodiments, the system 100 determines the glucose exposure over a time period based on the glucose data received at the predetermined interval. In at least one embodiment, the glucose exposure over a time period may be an average of the glucose data received at the predetermined interval over the course of the time period.

In many embodiments, the time period (or time interval) may be an overall amount of time from which the glucose exposure is being measured. For example, in one embodiment, the system 100 may determine the glucose exposure at the time 8:00 AM (the particular hour). Continuing with the example, in some embodiments, the time period may be from 00:00 AM to 8:00 AM, such that the system 100 determines the glucose exposure for the time period.

In another example, in at least one embodiment, the system 100 may determine the glucose exposure at the time 8:00 AM (the particular hour), and the time period may be one hour. Continuing with this example, the system 100 may determine the glucose exposure for each time period, and determine the glucose exposure at 8:00 AM by summing up the individual glucose exposures for each hour (or other increment of time) throughout the day. In one or more embodiments, the time period may range from one second to one day (such as, e.g., 15 minutes, 30 minutes, 1 hour, 3 hours, 1 day, etc.).

For example, in one embodiment, the predetermined interval may be one minute, and the time period may be thirty minutes, such that the system 100 receives glucose data thirty times within the time period. Continuing with the example, in at least one embodiment, the system 100 may calculate the average of the thirty glucose data points to determine the glucose exposure over the period of time. In an alternate embodiment, the system 100 may calculate a weighted average of the thirty glucose data points, such that the later received glucose data points have more weight than the earlier received glucose data points.

In a further embodiment, the system 100 may calculate a running total of glucose exposure through a twenty-four hour day by adding the determined glucose exposures over the time periods throughout the twenty-four hours. For example, in one embodiment, if the time period is sixty minutes, and the twenty-four hour day begins at midnight (00:00 AM), the system 100 may add each glucose exposure (in units of measurement) for each sixty minute time period over the course of the twenty-four hour day, so that, at a particular hour (e.g., 9:00 AM), the system 100 may determine the total glucose exposure for the user for the day at 9:00 AM.

In one or more embodiments, the system may be configured to compensate for a disconnected sensor and may use one or more smoothing algorithms (or the like) to fill in or approximate glucose exposure for an hour (or other suitable time period). For example, if a user is sleeping and is not wearing a sensor, the system may use historical or other data to estimate the user's glucose exposure while the sensor is disconnected.

At step 322, in multiple embodiments, if a Bluetooth radio is not connected to the sensor 104, the system 100 determines an average glucose exposure for the particular hour based on historical data. In this embodiment, since the system 100 is not connected to the sensor 104, the system 100 may not be able to receive current glucose data at the predetermined interval from the sensor 104. In many embodiments, the system 100 may store historical glucose data such that the system 100 may retrieve historical glucose data from previous days and utilize the historical data in the present average glucose exposure determination. In one or more embodiments, the utilization of the historical data allows the system 100 to continue to calculate the total glucose exposure and display the glucose exposure as a percentage of the target glucose level for the particular hour. In at least one embodiment, the historical data may include particular hour information, such that the system 100 may incorporate historical data from the same particular hour as the particular hour glucose data that is missing due to the system 100 not being connected to the sensor 104.

For example, in one embodiment, the Bluetooth radio may not be connected to the sensor 104 from 2:00 PM to 3:00 PM. Continuing with the example, in several embodiments, the system 100 may retrieve stored historical data from 2:00 PM to 3:00 PM from previous days, and average the stored historical data for the particular hour to get an average glucose exposure for the particular hour based on historical data. In an alternative embodiment, the system 100 may determine a weighted average for the glucose exposure for the particular hour based on historical data, such that the more recent historical data is given more weight than the older historical data, because the more recent historical data is more likely to be more accurate to the actual current glucose exposure.

In at least one embodiment, if the system 100 does not receive the glucose data from the sensor 104 at the particular interval, the system 100 may apply one or more smoothing algorithms once the system 100 is reconnected to the sensor 104, to back fill the missing glucose data. In one or more embodiments, the one or more smoothing algorithms may include calculating an average glucose exposure based on the glucose data received before and after the system 100 stopped receiving glucose data from the sensor 104. For example, in one embodiment, if the system 100 did not receive glucose data for one predetermined interval, the system 100 may utilize immediately preceding glucose data for at least one predetermined interval and immediately succeeding glucose data for at least one predetermined interval, and average the at least two glucose data points together to determine the missing glucose data for the predetermined interval. In at least one embodiment, the system 100 may utilize multiple immediately preceding glucose data points and multiple immediately succeeding glucose data points to determine the missing glucose data for the predetermined interval. In many embodiments, the user's glucose exposure does not vary much from one predetermined interval to the next, so the system 100 is able to take an average from the glucose data from preceding and succeeding glucose data to fill in a missing glucose data point with a high level of accuracy.

In one or more embodiments, the system 100 may utilize a combination of historical data and an average of recent data to determine missing glucose data points. For example, in one embodiment, if the system 100 is missing a glucose data point for 10:00 AM, the system 100 may retrieve historical glucose exposure data for 10:00 AM for the user, as well as calculate an average of recent preceding and succeeding glucose data, and determine or estimate the missing glucose data point from a combination of the historical glucose exposure data and the average of recent preceding and succeeding glucose data. In a further embodiment, the system 100 may also utilize other users' glucose exposure data to determine missing glucose data points. In this further embodiment, the system 100 may recognize other users as similar to the user with missing glucose exposure data, based on similarities in the users' profiles, such as the users' age, gender, height, weight, similarity in glucose exposure, and other similar factors.

In various embodiments, the system 100 may notify the user if the system 100 determines that the user's glucose exposure is higher or lower than the target glucose level for a particular hour by a more than a certain percentage. For example, in at least one embodiment, the system 100 may notify the user if the user's glucose exposure is ten percent (or more) greater than or less than the user's target glucose level for a particular hour. In many embodiments, the system 100 may notify the user via displaying a message on the device 106 or causing a push notification, SMS message, email, or other similar communication to display on or transmit to a secondary device.

In one or more embodiments, if the user's glucose exposure is greater than the user's glucose target for a particular hour, the system 100 may make recommendations to the user so that the user's glucose exposure may decrease in forthcoming hour(s). In some embodiments, the recommendations may include, but are not limited to, eating low-carbohydrate foods for the user's next meal, exercising, including a specific intensity level of exercising (such as, e.g., walking, jogging, running) taking insulin (for diabetic users), including rapid-acting insulin, short-acting insulin, intermediate-acting insulin, mixed-insulin, and long-acting insulin, or a combination of recommendations. In one embodiment, if the user has indicated to the system that the user's goal is to intake carbohydrates in preparation for future physical activity (such as, e.g., running a marathon), the system 100 may not notify the user if the user's glucose exposure exceeds the glucose target for a particular hour.

In multiple embodiments, the if the user's glucose exposure is less than the user's target glucose level for a particular hour by a certain amount, the system 100 may recommend the user take an action to increase the user's glucose exposure. In some embodiments, situations in which the system 100 may notify the user to increase the user's glucose exposure may include, but is not limited to, the user ingesting carbohydrates in preparation for a physical activity (such as, e.g., a triathlon), hypoglycemia, or other situations in which the user's glucose exposure is lower than the target glucose level for a particular hour. In many embodiments, the system 100 may recommend to a user to eat a carbohydrate-rich meal or snack to increase the user's glucose exposure if the user's glucose exposure is less than the target glucose level for a particular hour. For example, in one embodiment, a user may indicate to the system 100 that the user is attempting to reach or surpass the target glucose level for a particular hour in preparation to run a marathon, and so if the user's glucose exposure is five percent lower than the target glucose level for a particular hour, the system 100 may notify the user and recommend the user ingest carbohydrates. In at least one embodiment, the system 100 may recommend the user seek medical treatment, such as but not limited to, going to an emergency room or calling an ambulance, or other similar medical treatment, if the user's glucose exposure is low enough to be considered hypoglycemic.

Figure 4:
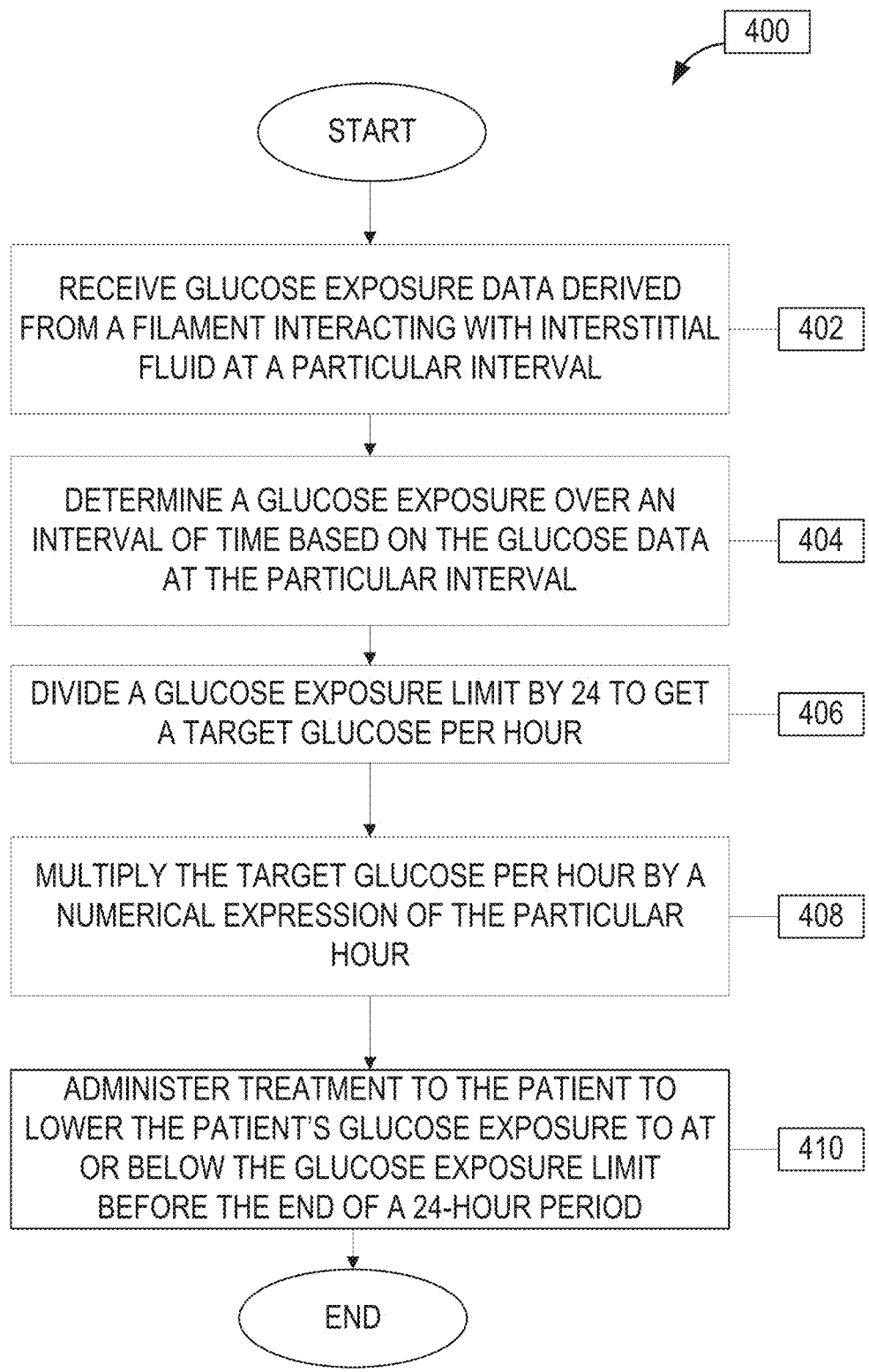
FIG. 4 is a flowchart of an exemplary glucose exposure diagnostic and treatment process, according to one embodiment of the present disclosure.

As shown in FIG. 4, an exemplary glucose exposure diagnostic and treatment process 400 is described, according to one embodiment of the present disclosure. In various embodiments, a user may first connect the sensor 104 to the user's body, such that the glucose sensor 120 is interacting with the interstitial fluid or otherwise determining a level of glucose within the patient's blood. In some embodiments, process 400 includes receiving glucose exposure data derived from a filament interacting with interstitial fluid at a particular interval (step 402), determining a glucose exposure over an interval of time based on the glucose data at the particular interval (step 404), dividing a glucose exposure limit by 24 to get a glucose exposure limit per hour (step 406), multiplying the glucose exposure limit per hour by a numerical expression of the particular hour (408), and administering treatment to the patient to lower the patient's glucose exposure to at or below the glucose exposure limit before the end of a 24-hour period (step 410). Steps 402, 404, 406, and 408 are substantially similar to steps 202, 206, 212, and 216 as described herein. For the sake of brevity, steps 402, 404, 406, and 408 will not be described here, but reference is made to steps 202, 206, 212, and 216 for descriptions of these steps.

As shown in step 410, in several embodiments, the system 100 may recommend, prescribe, and/or administer treatment to a patient to lower the patient's glucose exposure to at or below the glucose exposure limit (e.g., before the end of a 24-hour period). In many embodiments, suitable treatments may include prescribing and/or administering medications, exercising, dieting, or other similar treatments.

In multiple embodiment, the system 100 may be utilized to treat diabetes. In this embodiment, the system 100 may administer or recommend the patient be administered insulin or recommend the patient be administered insulin if the patient's glucose exposure exceeds the target glucose level for a particular hour.

In various embodiments, the system 100 may be utilized to treat nonalcoholic fatty liver disease and/or nonalcoholic steatohepatitis. In some embodiments, patients with nonalcoholic fatty liver disease and/or nonalcoholic steatohepatitis may limit glucose intake to decrease the amount of fat stored in the patient's liver. In one or more embodiments, upon a patient's current glucose exposure exceeding the target glucose level for a particular hour, the system 100 may administer or recommend the patient be administered treatments including but not limited to, insulin, insulin-sensitizing drugs (such as, e.g., pioglitazone), vitamin E, exercise, low-carbohydrate diet, and/or weight loss medication, to treat nonalcoholic fatty liver disease and/or nonalcoholic steatohepatitis.

In many embodiments, the system 100 may be utilized to treat obesity in a patient. In at least one embodiment, limiting glucose exposure may cause an obese patient to lose weight. In some embodiments, upon a patient's current glucose exposure exceeding the target glucose level for a particular hour, the patient may be administered weight loss medications (such as, e.g., semaglutide), dietary advice (such as, e.g., eating a low-carb meal), recommended exercise, and/or other similar treatments.

In several embodiments, the system 100 may be utilized to prevent a pre-diabetic patient to converting to type-II diabetes. In one or more embodiments, the system 100 may, upon a patient's current glucose exposure exceeding the target glucose level for a particular hour, the patient may be administered a low dosage of insulin, weight loss medication, dietary advice, recommended exercise, and/or other similar treatments.

From the foregoing, it will be understood that various aspects of the processes described herein are software processes that execute on computer systems that form parts of the system. Accordingly, it will be understood that various embodiments of the system described herein are generally implemented as specially-configured computers including various computer hardware components and, in many cases, significant additional features as compared to conventional or known computers, processes, or the like, as discussed in greater detail herein. Embodiments within the scope of the present disclosure also include computer-readable media for carrying or having computer-executable instructions or data structures stored thereon. Such computer-readable media can be any available media which can be accessed by a computer, or downloadable through communication networks. By way of example, and not limitation, such computer-readable media can comprise various forms of data storage devices or media such as RAM, ROM, flash memory, EEPROM, CD-ROM, DVD, or other optical disk storage, magnetic disk storage, solid state drives (SSDs) or other data storage devices, any type of removable nonvolatile memories such as secure digital (SD), flash memory, memory stick, etc., or any other medium which can be used to carry or store computer program code in the form of computer-executable instructions or data structures and which can be accessed by a computer.

When information is transferred or provided over a network or another communications connection (either hardwired, wireless, or a combination of hardwired or wireless) to a computer, the computer properly views the connection as a computer-readable medium. Thus, any such a connection is properly termed and considered a computer-readable medium. Combinations of the above should also be included within the scope of computer-readable media. Computer-executable instructions comprise, for example, instructions and data which cause a computer to perform one specific function or a group of functions.

Those skilled in the art will understand the features and aspects of a suitable computing environment in which aspects of the disclosure may be implemented. Although not required, some of the embodiments of the claimed systems and processes may be described in the context of computer-executable instructions, such as program modules or engines, as described earlier, being executed by computers in networked environments. Such program modules are often reflected and illustrated by flow charts, sequence diagrams, exemplary screen displays, and other techniques used by those skilled in the art to communicate how to make and use such computer program modules. Generally, program modules include routines, programs, functions, objects, components, data structures, application programming interface (API) calls to other computers whether local or remote, etc. that perform particular tasks or implement particular defined data types, within the computer. Computer-executable instructions, associated data structures and/or schemas, and program modules represent examples of the program code for executing steps of the methods disclosed herein. The particular sequence of such executable instructions or associated data structures represent examples of corresponding acts for implementing the functions described in such steps.

Those skilled in the art will also appreciate that the claimed and/or described systems and methods may be practiced in network computing environments with many types of computer system configurations, including personal computers, smartphones, tablets, hand-held devices, multi-processor systems, microprocessor-based or programmable consumer electronics, networked PCs, minicomputers, mainframe computers, and the like. Embodiments of the claimed systems and processes are practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing various aspects of the described operations, which is not illustrated, includes a computing device including a processing unit, a system memory, and a system bus that couples various system components including the system memory to the processing unit. The computer will typically include one or more data storage devices for reading data from and writing data to. The data storage devices provide nonvolatile storage of computer-executable instructions, data structures, program modules, and other data for the computer.

Computer program code that implements the functionality described herein typically comprises one or more program modules that may be stored on a data storage device. This program code, as is known to those skilled in the art, usually includes an operating system, one or more application programs, other program modules, and program data. A user may enter commands and information into the computer through keyboard, touch screen, pointing device, a script containing computer program code written in a scripting language or other input devices (not shown), such as a microphone, etc. These and other input devices are often connected to the processing unit through known electrical, optical, or wireless connections.

The computer that effects many aspects of the described processes will typically operate in a networked environment using logical connections to one or more remote computers or data sources, which are described further below. Remote computers may be another personal computer, a server, a router, a network PC, a peer device or other common network node, and typically include many or all of the elements described above relative to the main computer system in which the systems and processes are embodied. The logical connections between computers include a local area network (LAN), a wide area network (WAN), virtual networks (WAN or LAN), and wireless LANs (WLAN) that are presented here by way of example and not limitation. Such networking environments are commonplace in office-wide or enterprise-wide computer networks, intranets, and the Internet.

When used in a LAN or WLAN networking environment, a computer system implementing aspects of the systems and processes is connected to the local network through a network interface or adapter. When used in a WAN or WLAN networking environment, the computer may include a modem, a wireless link, or other mechanisms for establishing communications over the wide area network, such as the Internet. In a networked environment, program modules depicted relative to the computer, or portions thereof, may be stored in a remote data storage device. It will be appreciated that the network connections described or shown are exemplary and other mechanisms of establishing communications over wide area networks or the Internet may be used.

While various aspects have been described in the context of a preferred embodiment, additional aspects, features, and methodologies of the claimed systems and processes will be readily discernible from the description herein, by those of ordinary skill in the art. Many embodiments and adaptations of the disclosure and claimed systems and processes other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed systems and processes. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed systems and processes. In addition, some steps may be carried out simultaneously, contemporaneously, or in synchronization with other steps.

The embodiments were chosen and described in order to explain the principles of the claimed systems and processes and their practical application so as to enable others skilled in the art to utilize the systems and processes and various embodiments and with various modifications as are suited to the particular use contemplated. Alternative embodiments will become apparent to those skilled in the art to which the claimed systems and processes pertain without departing from their spirit and scope. Accordingly, the scope of the claimed systems and processes is defined by the appended claims rather than the foregoing description and the exemplary embodiments described therein.

What is claimed is:

1. A method for treating glucose over exposure comprising:
   receiving indications of glucose levels of a patient via a filament interacting with interstitial fluid on a particular interval;
   determining an average glucose level for a particular hour by averaging one or more indications of the glucose levels of the patient received during the particular hour;
   determining a current glucose exposure for the particular hour by summing the average glucose level for the particular hour with a summation of average glucose levels of the patient for hours preceding the particular hour in a 24-hour period;
   determining a target glucose level for the particular hour by multiplying a glucose exposure limit per hour by a numerical expression of the particular hour; and
   if the current glucose exposure for the particular hour exceeds the target glucose level for the particular hour, administering treatment to the patient to lower the patient's glucose exposure level to at or below a 24-hour glucose exposure limit before the end of the 24-hour period.

2. The method for treating glucose over exposure of claim 1, wherein the treatment comprises insulin.

3. The method for treating glucose over exposure of claim 2, wherein the treatment comprises one or more of the group comprising rapid-acting insulin, short-acting insulin, intermediate-acting insulin, mixed-insulin, or long-acting insulin.

4. The method for treating glucose over exposure of claim 1, wherein the treatment comprises pioglitazone.

5. The method of treating glucose over exposure of claim 1, wherein the treatment comprises one or more weight loss drugs.

6. The method of treating glucose over exposure of claim 1, wherein the treatment comprises one or more drugs to treat nonalcoholic fatty liver disease or nonalcoholic steatohepatitis.

7. The method of treating glucose over exposure of claim 1, wherein the glucose exposure limit per hour is based at least in part on historical glucose exposure data for the patient.

8. The method for treating glucose over exposure of claim 1, wherein the particular interval is 15 minutes.

9. The method for treating glucose over exposure of claim 8, wherein determining the average glucose level for the particular hour comprises averaging four of the indications of the glucose level of the patient received during the particular hour.

10. The method for treating glucose over exposure of claim 1, wherein the particular interval is 1 minute.

11. The method for treating glucose over exposure of claim 10, wherein determining the average glucose level for the particular hour comprises averaging sixty of the indications of the glucose level of the patient received during the particular hour.

12. The method of treating glucose over exposure of claim 1, wherein the 24-hour glucose exposure limit comprises a summation of the glucose exposure limit per hour for 24 hours.

13. The method for treating glucose over exposure of claim 12, wherein the average glucose levels of the patient for hours preceding the particular hour in the 24-hour period comprises at least one average glucose level based on historical data.

14. The method for treating glucose over exposure of claim 13, wherein the at least one average glucose level based on historical data comprises an average of average glucose levels for an hour immediately preceding the particular hour and an hour in a different 24-hour period.

15. The method for treating glucose over exposure of claim 13, wherein the at least one average glucose level based on historical data comprises an average of stored glucose exposure data for the particular hour for different 24-hour periods.

16. A method of diagnosing and treating glucose over exposure comprising:
receiving a current glucose exposure for a particular hour, wherein the current glucose exposure for the particular hour is determined by summing an average glucose level for the particular hour with a summation of average glucose levels of a patient for hours preceding the particular hour in a 24-hour period, wherein:
the average glucose level for the particular hour is determined by averaging one or more indications of a glucose level of the patient received during the particular hour; and
the one or more indications of the glucose level of the patient are derived from a filament interacting with interstitial fluid;
determining a target glucose level for the particular hour based on a glucose exposure limit; and
if the current glucose exposure for the particular hour exceeds the target glucose level for the particular hour, administering treatment to the patient to lower the patient's glucose exposure level to at or below the glucose exposure limit.

17. The method of diagnosing and treating glucose over exposure of claim 16, wherein the glucose exposure limit is a 24-hour glucose exposure limit.

18. The method of diagnosing and treating glucose over exposure of claim 16, wherein the glucose exposure limit is a glucose exposure limit for less than 24 hours.

19. The method for treating glucose over exposure of claim 16, wherein the treatment comprises one or more of the group comprising rapid-acting insulin, short-acting insulin, intermediate-acting insulin, mixed-insulin, or long-acting insulin.

20. The method of treating glucose over exposure of claim 16, wherein the treatment comprises one or more drugs to treat nonalcoholic fatty liver disease or nonalcoholic steatohepatitis.

* * * * *